United States Patent [19]

Lesher et al.

[11] 4,053,475
[45] Oct. 11, 1977

[54] N-[2-(PYRIDINYL)-4-PYRIMIDINYL]UREAS PREPARATION

[75] Inventors: George Y. Lesher, Rensselaer; Baldev Singh, East Greenbush, both of N.Y.

[73] Assignee: Sterling Drug Inc., New York, N.Y.

[21] Appl. No.: 704,519

[22] Filed: July 12, 1976

Related U.S. Application Data

[62] Division of Ser. No. 556,213, March 7, 1975, Pat. No. 4,008,235.

[51] Int. Cl.$^2$ .................. C07D 401/04; A61K 31/17; A61K 31/44
[52] U.S. Cl. .............................. 260/256.4 N; 424/251
[58] Field of Search ................................ 260/256.4 N

[56] References Cited

PUBLICATIONS

Brown, *Heterocyclic Compounds;* The Pyrimidines, Supp. I, 1970, Interscience, N.Y., pp. 259–261.

*Primary Examiner*—Donald G. Daus
*Assistant Examiner*—James H. Turnipseed
*Attorney, Agent, or Firm*—Robert K. Bair; B. Woodrow Wyatt

[57] ABSTRACT

N—$R_3$—N—$R_4$—N'—(2—Q—5—$R_1$—6—$R_2$—4-Pyrimidinyl)ureas which are useful as anti-allergic agents are prepared by reacting a 2—Q—4—RNH—5—$R_1$—6—$R_2$-pyrimidine with an $R_4$'-isocyanate and reacting the intermediate product with 1,1'-carbonyldiimidasole.

3 Claims, No Drawings

N-[2-(PYRIDINYL)-4-PYRIMIDINYL]UREAS PREPARATION

CROSS-REFERENCE TO RELATED APPLICATIONS

This application is a division of copending Application Ser. No. 556,213, filed Mar. 7, 1975, now U.S. Pat. No. 4,008,235, issued Feb. 15, 1977.

The intermediate 2-Q-4-(RNH)-5-$R_1$-6-$R_2$-pyrimidines (II) disclosed herein are disclosed and claimed in copending U.S. Patent Application Serial No. 555,067, filed Mar. 3, 1975, now U.S. Pat. No. 4,018,770.

BACKGROUND OF THE INVENTION a. Field of the Invention

This invention relates to pyrimidinyl-ureas which are useful as anti-allergic agents, and to their preparation.

b. Description of the Prior Art

Dyer et al., J. Org. Chem. 27, 982 (1962), show the preparation of 1-phenyl-3-(4-pyrimidinyl)urea, which alternatively can be named N-phenyl-N'-(4-pyrimidinyl)urea, by reacting 4-aminopyrimidine with phenyl isocyanate.

The Laboratories Leurquin French Demande (Patent Publication) 2,036,922, February 5, 1971 [Chem. Abstrs. 75, 118335q (1971)] relates to "2-(substituted ureido)-pyrimidines" of formula (1)

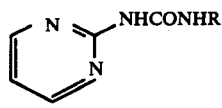

"where R is H, alkyl, alkenyl, cycloalkyl or aryl, having cicatrizant, fatigue lessening, sedative, anti-senescent and hypnotic sleep potentiating action". These compounds, except where R is H, were prepared "by treating 2-aminopyrimidine (2) with an isocyanate", e.g., (2) "was heated with PhNCO to give" (1) (R=Ph). A mixture of urea, 2-aminopyrimidine, and AcOH was kept at 0.5 hr. at 180° to give (1) where R is H.

SUMMARY OF THE INVENTION

In its composition aspect, the invention relates to certain N—$R_3$—N—$R_4$—N'—R-N'—(2—Q—5—$R_1$—6—$R_2$—4-pyrimidinyl)ureas (I), which are useful as anti-allergic agents.

The invention in its process aspects comprises reacting a 2—Q—4—RNH—5—$R_1$—6—$R_2$-pyrimidine (II) with a carbamylating agent selected from: an $R_4'$-isocyanate of the formula $R_4'N=C=O$ to produce N—$R_4'$—N'—R—N'—(2—Q—5—$R_1$—6—$R_2$—4-pyrimidinyl)urea (IA); an N—$R_3'$—N—$R_4'$-carbamyl halide of the formula $R_3'R_4'NC(=O)$-halogen to produce N—$R_3'$—N—$R_4'$—N'—R—N'— (2—Q—5—$R_1$—6—$R_2$—4-pyrimidinyl)urea (IB); or, 1,1'-carbonyldiimidazole to produce first N-(2—Q—5—$R_1$—6—$R_2$—4-pyrimidinyl)-N-R-imidazole-1-carboxamide and then reacting said 1-carboxamide with $R_3R_4NH$ to produce I.

DETAILED DESCRIPTION INCLUSIVE OF PREFERRED EMBODIMENTS

The invention in its composition aspect resides in the compounds having formula I

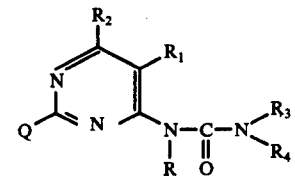

where Q is 4- or 3- or 2-pyridinyl or 4- or 3- or 2-pyridinyl having one or two lower-alkyl substituents or N-oxide thereof, R is hydrogen or lower-alkyl, $R_1$ is hydrogen, lower-alkyl or cyano, $R_2$ is hydrogen or lower-alkyl, $R_3$ is hydrogen, loweralkyl or lower-hydroxyalkyl, and, $R_4$ is hydrogen, lower-alkyl, lower-hydroxyalkyl, lower-alkenyl or lower-cycloalkyl. The compounds of formula I are useful as anti-allergic agents, as determined by standard pharmacological evaluation procedures. Preferred embodiments are those having formula I where R, $R_1$, $R_2$ and $R_3$ are each hydrogen, Q is 4- or 3-pyridinyl and $R_4$ is alkyl having from one to four carbon atoms.

The invention in a process aspect for preparing the compounds of formula I comprises reacting a 2—Q—4—RNH-5—$R_1$—6—$R_2$-pyrimidine having formula II

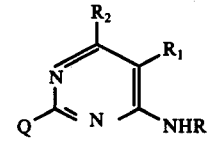

where Q, R, $R_1$ and $R_2$ have the meanings given above for formula I, with a carbamylating agent selected from: an $R_4'$-isocyanate of the formula $R_4'N=C=O$ to produce the compound of formula IA

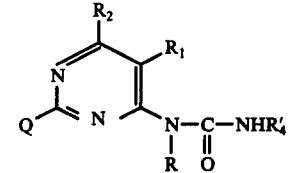

where $R_4'$ is lower-alkyl, lower-alkenyl or lower-cycloalkyl; an N—$R_3'$—N—$R_4'$-carbamyl halide of the formula $R_3'R_4'NC(=O)$-halide to produce the compound of formula IB

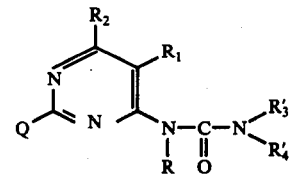

where $R_3'$ is lower-alkyl, and $R_4'$ is lower-alkyl, lower-alkenyl or lower-cycloalkyl; and, 1,1'-carbonyldiimidazole to produce N-(2—Q—5—$R_1$—6—$R_2$—4-pyrimidinyl)—N—R—imidazole-1-carboxamide and then reacting said 1-carboxamide with $R_3R_4NH$ to produce a compound of formula I, where $R_3$ and $R_4$ have the meanings given above for formula I.

The term "lower-alkyl" as used herein, e.g., as one of the meanings for R, $R_1$, $R_2$, $R_3$, $R_4$, or $R_5$ or as a substituent for Q in formula I, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of Q in formulas I, II or III where Q is 4-, 3- or 2-pyridinyl having one or two lower-alkyl substituents are the following [note that "pyridinyl" as used herein is the same as "pyridyl", the former now being the preferred term used in Chemical Abstracts]: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl) 4-methyl-2-pyridinyl, 6-methyl-2-pyridinyl, 2,3-dimethyl-4-pyridinyl, 2,6-dimethyl-4-pyridinyl, 4,6-dimethyl-2-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-di-isopropyl-4-pyridinyl, 2,6-di-n-hexyl-4-pyridinyl, and the like.

The term "lower-carbalkoxy", as used herein, e.g., as one of the meanings for Ac in formula III hereinbelow, means carbalkoxy radicals where the alkoxy portion can be straight- or branch-chained and has from one to six carbon atoms, as illustrated by carbomethoxy, carbethoxy, carbo-n-propoxy, carbisopropoxy, carbo-n-butoxy, carbo-tert.-butoxy and carbo-n-hexoxy.

The term "lower-alkanoyl", as used herein, e.g., as one of the meanings for Ac in formula III hereinbelow, means alkanoyl radicals having from two to six carbon atoms, including the straight- and branch-chained radicals, illustrated by acetyl, propionyl (n-propanoyl), butyryl (n-butanoyl), isobutyryl (2-methyl-n-propanoyl) and caproyl (n-hexanoyl).

Ther term "lower-hydroxyalkyl", as used herein, e.g., as one of the meanings for $R_3$ and $R_4$ in formula I, means hydroxyalkyl radicals having from two to six carbon atoms and having its hydroxy group and its free valence bond (or connecting linkage) on different carbon atoms, illustrated by 2-hydroxyethyl, 2-hydroxypropyl, 3-hydroxypropyl, 2-hydroxy-2-methylpropyl, 3-hydroxypropyl, 2-hydroxy-1,1-dimethylethyl, 4-hydroxybutyl, 5-hydroxyamyl, 6-hydroxyhexyl, and the like.

The term "lower-alkenyl", as used herein, e.g., as one of the meanings for $R_4$ in formula I or for $R_4'$ in formulas IA or IB, means alkenyl radicals having from three to six carbon atoms and having its free valence bond (or connecting linkage) on a carbon atom other than one containing the double bond, illustrated by $CH_2CH=CH_2$ (i.e., allyl), $CH_2C(CH_3)=CH_2$, $CH_2CH=CHCH_3$, $CH_2CH=CHCH_2CH_3$, $CH_2CH=CHCH_2CH_2CH_3$, $CH_2CH_2CH=CHCH_3$, $CH_2CH=C(CH_3)CH_3$, and the like.

The term "lower-cycloalkyl", as used herein, e.g., as one of the meanings for $R_4$ in formula I or for $R_4'$ in formulas IA or IB, means cycloalkyl radicals having from three to six ring-carbon atoms, illustrated by cyclopropyl, cyclobutyl, cyclopentyl and cyclohexyl.

Also, the compounds of formula I are useful both in the free base form and in the form of acid-addition salts; and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, medicinally acceptable salts, that is, salts whose anions are relatively innocuous to the animal organism in medicinal doses of the salts, so that the beneficial anti-allergic properties inherent in the free base are not vitiated by side effects ascribable to the anions. In practicing the invention, it was found convenient to form the hydrochloride, methanesulfonate or lactate. However, other appropriate medicinally acceptable salts within the scope of the invention are those derived from mineral acids such as phosphoric acid, sulfamic acid, and sulfuric acid; and organic acids such as acetic acid, citric acid, tartaric acid, ethanesulfonic acid, benzenesulfonic acid, p-toluenesulfonic acid, cyclohexylsulfamic acid, quinic acid, and the like, giving the phosphate, sulfate, acetate, citrate, tartrate, ethanesulfonate, benzenesulfonate, p-toluenesulfonate, cyclohexylsulfamate and quinate, respectively.

The acid-addition salts or said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although medicinally acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The molecular structures of the composition aspect (I) of the invention were assigned on the basis of evidence provided by infrared, ultraviolet, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of chemistry to make and use the same, as follows:

The preparation of the compounds of formula IA is carried out by reacting a 2—Q—4—RNH—5—$R_1$—6—$R_2$-pyrimidine (II) with a carbamylating agent of the formula $R_4'N=C=O$, that is, an $R_4'$-isocyanate, where Q, R, $R_1$ and $R_2$ have the meanings given for formula I and $R_4'$ -is lower-alkyl, lower-alkenyl or lower-cycloalkyl. This reaction is conveniently carried out by mixing said reactants, preferably in a molar ratio of 1:1 with stirring at about 20° C. to 150° C., preferably about 20° C. to 60° C., preferably using a suitable inert solvent and using the said 4-RNH-pyrimidine (II) as its alkali metal salt, preferably the sodium salt which is conveniently prepared using sodium hydride dispersed in mineral oil. Prepared solvents are aprotic solvents, especially dimethyl sulfoxide and dimethylformamide. Other inert aprotic solvents which can be used include dimethylthiourea, tetramethylurea, dimethylactamide, hexamethylphosphoramide, N-methylpyrrolidine, and the like. The reaction also can be run by heating II in free base form wih an $R_4'$-isocyanate at about 100°–200° C. in an inert solvent, e.g., said aprotic solvents and also toluene, xylene, chlorobenzene, anisole, and the like; however, the reaction takes longer.

The reaction of II with a carbamylating agent of the formula R₃'R₄'NC(=O)-halide, preferably where halide is chloride, to produce IB is conveniently carried out by mixing the reactants, II preferably as its sodium salt in said inert solvent, at room temperature or when chilled in an ice bath.

The reaction of II with 1,1'-carbonyldiimidazole to produce N-[2—Q—5—R₁—6—R₂-4pyrimidinyl]—N—R—imidazole-1-carboxamide is carried out preferably by mixing the reactants, II preferably as its sodium salts, in said inert solvent at room temperature and then said -1-carboxamide, without isolation, is reacted, also preferably at room temperature, with R₃R₄NH. When R₃ and R₄ are each H, that is, R₃R₄NH is ammonia, it is convenient to provide the ammonia in the form of aqueous ammonium hydroxide or, alternatively, gaseous ammonia can be bubbled into the reaction mixture.

The reaction of the compound of formula I where Q is other than pyridinyl N-oxide with an oxidizing agent to produce the compound of formula I where Q is pyridinyl N-oxide is carried out by reacting compound of formula I where Q is pyridinyl with an oxidizing agent capable of converting pyridines to pyridine-N-oxides, preferably with a per acid, e.g., peracetic acid, perbenzoic acid, 3-chloroperbenzoic acid, and the like, or with other oxidizing agents, e.g., hydrogen peroxide, in the presence of a suitable solvent inert under the reaction conditions, e.g. acetic acid, chloroform, and the like. The reaction is conveniently run by mixing the reactants carefully at room temperature (about 20°-25° C.) up to about 40°-50° C., preferably with stirring, and then heating the reaction mixture on a steam bath to ensure completion of the reaction.

The compounds of formula II are prepared by various procedures which are illustrated generally in the following paragraphs and are further illustrated hereinbelow in the specific exemplary disclosure.

The preparation of the compounds of formula II where R₁ and R₂ are each hydrogen and R is hydrogen is conveniently carried out by heating a pyridinecarboxamidine of the formula, Q—C(=NH)NH₂, with a β-(lower-alkoxy)-acrylonitrile, preferably β-ethoxyacrylonitrile to produce the 4-amino-2—Q—pyrimidine.

The preparation of the compounds of formula II where R₂ is lower-alkyl, R₁ is hydrogen or lower-alkyl and R is hydrogen are readily produced by reacting a pyridinecarboxamidine of the formula, Q—C(=NH)NH₂, with a lower-alkyl β-oxoalkanoate of the formula, R₂—COCH(R₁)—COO—(lower-alkyl) to produce 2—Q—5—R₁—6—R₂—4—pyrimidinol, reacting the 4-pyrimidinol with a halogenating agent to produce 4-halo—2—Q—5—R₁—6—R₂-pyrimidine, reacting the 4-halo compound with hydrazine to produce 4-hydrazino—2—Q—5—R₁—6—R₂-pyrimidine and catalytically hydrogenating the 4-hydrazino compound in the presence of a suitable catalyst, e.g., Raney nickel, to produce 4-amino—2—Q—5—R₂—6—R₂—pyrimidine.

The preparation of the compounds of formula II where R₂ is hydrogen, R₁ is methyl and R is hydrogen is carried out by reacting a pyridinecarboxamidine of the formula, Q—C(=NH)NH₂, with α-piperidinomethylacrylonitrile to produce 4-amino-5-methyl-2-Q-pyrimidine. Optionally, α-piperidinomethylacrylonitrile can be replaced by other α-[(BN)methyl]acrylonitriles where BN is lower-tertiary-amino such as di-(lower-alkyl)amino, e.g., (CH₃)₂N, (C₂H₅)₂N, and the like, or other saturated N-heteromonocyclic radicals, having 5 or 6 ring atoms, e.g. pyrrolidino, N-methylpiperazino, 2-methylpiperidino, and the like.

The preparation of the compounds of formula II where R₂ is hydrogen, R₂ is cyano and R is hydrogen is carried out by reacting a pyridinecarboxamidine of the formula, Q—C(=NH)NH₂, with a (lower-alkoxy)methylenemalonitrile, preferably ethoxymethylenemalonitrile, to produce 4-amino-5-cyano-2-Q-pyrimidine.

The preparation of the compounds of formula II where R₂ is hydroxy or hydrogen, R₁ is hydrogen or lower-alkyl and R is hydrogen are carried out by reacting a pyridine-carboxamidine of the formula, Q-C(=NH)NH₂, with a compound of the formula NC-CH(R₁)COO-(lower-alkyl) to produce 4-amino-6-hydroxy-5-R₁—2—Q-pyrimidine, halogenating this 6-hydroxy compound to produce 4-amino-6-halo—5—R-1—2—Q-pyrimidine and catalytically hydrogenating the 6-halo, preferably, 6-chloro compound using about 50 p.s.i. of hydrogen in the presence of palladium-on-charcoal catalyst to remove the halo substituent and to produce 4-amino-5—R₁—2—Q-pyrimidine.

The intermediate pyridinecarboxamidines of the formula, Q-C(=NH)NH₂, are generally known compounds which are prepared by conventional means.

The preparation of the compounds of formula II where R is hydrogen and Q is pyridinyl N-oxide are pepared by reacting the 4-acylamino compounds having formula III

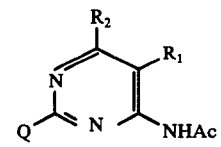

III where Q is other than pyridinyl N-oxide and Q, R₁ and R₂ are defined as in formula I and Ac is lower-alkanoyl or lower-carbalkoxy, with an oxidizing agent capable of converting pyridines to pyridine-N-oxides by the procedure described above for oxidizing the compounds of formula I where Q is other than pyridinyl N-oxide to produce the corresponding compounds of formula I where Q is pyridinyl N-oxide and then hydrolyzing, as illustrated hereinbelow, the 4-acylamino compound (IV, n is 1) to produce the 4-amino compound (II, R is hydrogen and Q is a pyridinyl N-oxide group).

The compound of formula III where Q is other than pyridinyl N-oxide is prepared by acylating the corresponding compound of formula II where Q is other than pyridinyl N-oxide and R is hydrogen, that is, by reacting the said 4-amino compound (II) with a lower-alkanoylating agent or a lower-carbalkoxylating agent, e.g., a lower-alkanoyl halide, preferably chloride, a lower-alkanoic anhydride, a lower-alkyl haloformate, a lower-alkyl azidoformate, and the like, preferably in the presence of an acid acceptor, as illustrated hereinbelow.

The compound of formula II where R is lower-alkyl is prepared by reacting the corresponding 2—Q—4—halo—5—R₁—6—R₂— pyrimidine with a primary amine RNH₂ where R is lower-alkyl. This reaction is conveniently carried out in a lower-alkanol, with or without water; it is preferably run in refluxing ethanol or ethanol-water.

The following examples will further illustrate the invention without, however, limiting it thereto.

A. 4-AMINO-2-(PYRIDINYL)PYRIMIDINES AND INTERMEDIATES

A-1. 4-Amino-2-(4-pyridinyl)pyrimidine [same as 2-(4-pyridinyl)-4-pyrimidinamine] — To an ice cold and stirred solution of 172 g. of sodium methoxide in 800 ml. of methanol ws slowly added 304 g. of isonicotinamidine dihydrochloride; the resulting mixture ws stirred for fifteen minutes and filtered. The inorganic residue was washed with methanol and the filtrate plus washings were evaporated to dryness in vacuo on a steam bath to yield 288 g. of isonicotinamidine in free base form. A mixture of said isonicotinamidine and 150 g. of β-ethoxyacrylonitrile was heated in an oil bath at 130°–150° C. for about four hours, allowing the ethnol formed by the reaction to distill off. The remaining material was dissolved in 200 ml. of concentrated hydrochloric acid and 100 ml. of water, and the solution allowed to stand overnight at room temperature (about 20°–25° C.). The solution was treated with decolorizing charcoal, heated on a steam bath for thirty minutes, filtered and the filtrate basified with ammonium hydroxide. The resulting solid was collected, washed with cold water, air-dried, disgested with hot methanol, separated and air-dried to yield, as a tan powder, 105 g. of 4-amino-2-(4-pyridinyl)pyrimidine, m.p. 260°–262° C.

The hydrochloride salt of 4-amino-2-(4-pyridinyl)pyrimidine was prepared as follows: a mixture containing 10 g. of 4-amino-2-(4-pyridinyl)pyrimidine, 30 ml. of water and 20 ml. of concentrated hydrochloric acid was warmed to effect solution. To the warm solution was added isopropyl alcohol to tubidity (about 110 ml.) whereupon crystals started to separate. The mixture was cooled and the crystalline precipitate was collected, washed with isopropyl alcohol and ether and dried in vacuo at 80° C. to yield 9.5 g. of 4-amino-2-(4-pyridinyl)pyrimidine dihydrochloride as its monohydrate, m.p. 229° C. with decomposition.

A-2. 4-Amino-2-(3-pyridinyl)pyrimidine, m.p. 157°–159° C., 45 g., was prepared following the procedure described in Example A-1 using 72 g. of nicotinamidine dihydrochloride, 54 g. of sodium methoxide, 400 ml. of methanol, 60 g. of β-ethoxyacrylonitrile and a heting period of three hours at 100°–125° C.

A-3. 6-Methyl-2-(4-pyridinyl)-4-pyrimidinol — A mixture containing 15.8 g. of isonicotinamidine hydrochloride, 16.8 g. of sodium methoxide, 17 g. of ethyl acetoacetate and 100 ml. of ethanol was refluxed with stirring for seven hours and then evaporated to dryness. The residue was dissolved in water and the aqueous solution made acidic with acetic acid. The resulting solution was collected, washed with water, dried and recrystallized from ethanol to yield 6.7 g. of 6-methyl-2-(4-pyridinyl)-4-pyrimidinol, m.p. 236°–238° C.

A-4. 6-n-Propyl-2-(4-pyridinyl)-4-pyrimidinol — To an ice cooled solution containing 500 ml. of methanol and 16 g. of sodium methoxide was added 47.4 g. of isonicotinamidine hydrochloride; the mixture was stirred for fifteen minutes and filtered to remove the precipitated sodium chloride; the filtrate was concentrated in vacuo; 56 g. of ethyl n-butrylacetate was added; and the resulting mixture was heated in an oil bath at 160°–180° C for three hours. After the reaction mixture had been cooled, the separated product was collected and recrystallized from ethanol to yield 38.9 g. of 6-n-propyl-2-(4-pyridinyl)-4-pyrimidinol, m.p. 173°–174° C.

A-5. 4-Chloro-6-methyl-2-(4-pyridinyl)pyrimidine — A mixture containing 26.5 g. of 6-methyl-2-(4-pyridinyl)-4-pyrimidinol, 27 g. of phenylphosphonic dichloride and 75 ml. of phosphorus oxychloride was refluxed for four hours and then poured onto ice. The resulting aqueous mixture was made basic with ammonium hydroxide. The product was extracted from the alkaline mixture using chloroform and the chloroform extract was concentrated in vacuo. The residue was filtered thru a silica gel column using ether as the solvent and eluent. Removal of the ether yielded 12.9 g. of 4-chloro-6-methyl-2-(4-pyridinyl)-pyrimidine, m.p. 128°–130° C.

A-6. 4-Hydrazino-6-methyl-2-(4-pyridinyl)pyrimidine — A solution containing 36 g. of 4-chloro-6-methyl-2-(4-pyridinyl)-pyrimidine, 100 ml. of ethanol and 20 ml. of hydrazine hydrate was refluxed on a steam bath for two hours and then evaporated to dryness. The residue was partitioned between water and chloroform. The chloroform layer was separated and the chloroform distilled off in vacuo to yield, as a yellow solid, 31.2 g. of 4-hydrazine-6-methyl-2-(4-pyridinyl)pyrimidine, m.p. 150°–152° C., which was used in the following step given in Example A-7. A 3.6 g. portion of this hydrazine was converted into its dicyclohexylsulfamate salt which was recrystallized from ethanol to yield 7.2 g. of said salt, m.p. >280° C. with decomposition.

A-7. 4-Amino-6-methyl-2-(4-pyridinyl)pyrimidine — A mixture containing 31 g. of 4-hydrazino-6-methyl-2-(4-pyridinyl)pyrimidine, 150 ml. of ethanol and 2 g. of Raney nickel was shaken under hydrogen (48 p.s.i.) and heated to 63° C. whereupon there was an uptake of 10.7 lbs. of hydrogen. The reaction mixture was cooled to room temperature and the catalyst was filtered off. The filtrate was concentrated in vacuo to yield on orange solid that was crystallized from isopropyl alcohol to yield, as tan crystals, 22.6 g. of 4-amino-6-methyl-2-(4-pyridinyl)pyrimidine, m.p. 192°–194° C.

A-8. 4-Amino-5-methyl-2(4-pyridinyl)pyrimidine — A mixture containing 15.8 g. of isonicotinamidine hydrochloride, 100 ml. of ethanol, 5.4 g. of sodium methoxide and 16.8 g. of α-(piperidinomethyl)acrylonitrile was stirred at room temperature for two hours and then refluxed overnight (about sixteen hours). The reaction mixture was then cooled and evaporated to dryness in vacuo. The residue ws diluted with water and the solid was collected, washed with water and recrystallized from isopropyl alcohol to yield 5.7 g. of 4-amino-5-methyl-2-(4-pyridinyl)pyrimidine, m.p. 224°–226° C. It was crystallized as its dimethanesulfonate, m.p. 210°–213° C., 6.5 g., by dissolving it in a minimum of hot isopropyl alcohol, adding 6.6 ml. of methanesulfonic acid, cooling the mixture, collecting the precipitated salt and drying it in vacuo at 80° C.

A-9. 4-Amino-2-(2-pyridinyl)pyrimidine — A mixture containing 12.2 g. of 2-pyridinecarboxamidine in 9.8 g. of β-ethoxyacrylonitrile was heated in an oil bath at 150°–160° C. for three hours. The solid residue was taken up in boiling isopropyl alcohol, the hot solution treated with decolorizing charcoal and filtered. To the hot filtrate was added 21 g. of methanesulfonic acid and the mixture chilled. The separated salt was recrystallized twice from isopropanol-ethanol and once from ethanol to yield 11.8 g. of 4-amino-2-(2-pyridinyl)-pyrimidine as its dimethanesulfonate, m.p. 184°–186° C.

Following the procedure described in Example A-1 but using in place of isonicotinamidine a molar equivalent quantity of the appropriate pyridinecarboxamidine, i.e., Q—C(=NH)NH$_2$, the 4-amino-2-Q-pyrimidines of Examples A-10 through A-13 are obtained:

A-10. 4-Amino-2-(2-methyl-4-pyridinyl)pyrimidine using 2-methylisonicotinamidine.

A-11. 4-Amino-2-(3-methyl-4-pyridinyl)pyrimidine using 3-methylisonicotinamidine. A-12. 4-Amino-2(2-ethyl-4-pyridinyl)pyrimidine using 2-ethylisonicotinamidine.

A-13. 4-Amino-2-(2,6-dimethyl-4-pyridinyl)pyrimidine using 2,6-dimethylisonicotinamidine.

A-14. 4-Amino-2-(4-pyridinyl)-6-pyrimidinol [alternatively named as 6-amino-2-(4-pyridinyl)-4-pyrimidinol] — A mixture containing 15.6 g. of isonicotinamidine hydrochloride, 11.3 g. of ethyl cyanoacetate, 1.8 g. of sodium methoxide and 100 ml. of ethanol was stirred at room temperature for thirty minutes and then refluxed for seven hours, followed by evaporation to dryness. To the residue was added 100 ml. of water and the mixture was then acidified by adding acetic acid. The solid was collected, dried in vacuo at 80° C., slurried in 100 ml. boiling ethanol and collected to yield 9.6 g. of 4-amino-2-(4-pyridinyl)-6-pyrimidinol, m.p. >350° C.

A-15. 4-Amino-2-(4-pyridinyl)-5-pyrimidinecarbonitrile — To a stirred solution containing 15.8 g. of isonicotinamidine hydrochloride, 6 g. of sodium methoxide and 200 ml. of methanol was added 14.2 g. of ethoxymethylenemalonitrile and the resulting mixture was stirred at room temperature overnight (about sixteen hours). The solid was collected, washed with water and recrystallized from methanol to yield 20.7 g. of 4-amino-2-(4-pyridinyl)-5-pyrimidinecarbonitrile, m.p. 253–255° C.

A-16. N-[2-(4-Pyridinyl)-4-pyrimidinyl]acetamide — A mixture containing 7 g. of 4-amino-2-(4-pyridinyl)-pyrimidine, 25 ml. of pyridine and 10 ml. of acetic anhydride was allowed to stand at room temperature overnight, and then boiled on a hot plate until all of the solid had dissolved. The reaction mixture was cooled to room temperature and poured onto ice. After the ice had melted, the white crystalline solid was collected, washed with water, dried in vacuo at 80° C. and recrystallized from ethanol to produce 3.8 g. of N-[2-(4-pyridinyl)-4-pyrimidinyl]acetamide, m.p. 218°–220° C.

A-17. N-[2-(4-Pyridinyl)-4-pyrimidinyl]hexanamide — A mixture containing 4 g. of 4-amine-2-(4-pyridinyl)-pyrimidine, 5 g. of n-hexanoyl chloride and 50 ml. of pyridine was allowed to stand at room temperature overnight and then poured onto the ice. After the ice had melted, 10 ml. of concentrated ammonium hydroxide was added and the cream colored solid was collected, washed with water, dried in vacuo and recrystallized from isopropyl alcohol to yield 6.2 g. of N-[2-(4-pyridinyl)-4-pyrimidinyl]hexanamide, m.p. 119°–120° C.

A-18. 2-Methyl-N-[2-(4-pyridinyl)-4-pyrimidinyl]-propanamide — A mixture containing 8.6 g. of 4-amino-2-(4-pyridinyl)pyrimidine, 50 ml. of pyridine and 10 ml. of isobutyryl chloride was allowed to stand at room temperature overnight and then poured into ice cold water. The solid was collected, washed with water, dried in vacuo at 80° C. and recrystallized from ethanol to yield 7.9 g. of 2-methyl-N-[2-(4-pyridinyl)-4-pyrimidinyl]propanamide, m.p. 215°–217° C.

A-19. n-Butyl N-[2-(4-pyridinyl)-4-pyrimidinyl]-carbamate — A mixture containing 9 g. of 4-amino-2-(4-pyridinyl)-pyrimidine, 10 ml. of n-butyl chloroformate and pyridine was kept in an ice bath for one hour and then at room temperature overnight. The reaction mixture was then poured into ice cold water; the solid was collected, washed with water, dried in vacuo at 80° C. and recrystallized from acetonitrile to yield 11.2 g. of n-butyl N-[2-(4-pyridinyl)-4-pyrimidinyl]carbamate, m.p. 180°–182° C.

A-20. Ethyl N-[2-(4-pyridinyl)-4-pyrimidinyl]-carbamate as its methanesulfonate, m.p. 198°–200° C., is obtained following the procedure described in Example A-19 but using in place of n-butyl chloroformate a molar equivalent quantity of ethyl chloroformate, and recrystallization from ethanol.

A-21. n-Butyl N-[2-(4-pyridinyl)-4-pyrimidinyl]-carbamate N-Oxide [It will be appreciated, in view of the definition of Q in formula I hereinabove, the N-oxide as used here and elsewhere in naming claimed compounds of the invention means the N-oxide of the 2-(pyridinyl) substituent, specifically the N-oxide of the 2-(4-pyridinyl) substituent in this Example A-21.] — To an ice cold solution containing 6 g. of n-butyl N-[2-(4-pyridinyl)-4-pyrimidinyl]carbamate and 100 ml. of chloroform was added 4.9 g. of 85% m-chloroperbenzoic acid and the resulting solution was allowed to stand at room temperature overnight. The excess acid was extracted with aqueous potassium carbonate and the remaining organic solution was collected to yield 5.8 g. of n-butyl N-[2-(4-pyridinyl)-4-pyrimidinyl]carbamate N-oxide which was combined with 1.9 g. of the same compound prepared in another run and the combined 7.7 g. of this compound was used without and further purification in the following Example A-22.

A-22. 4-Amino-2-(4-pyridinyl)-4-pyrimidine N-Oxide — A mixture containing 7.7 g. of n-butyl N-[2-(4-pyridinyl)-4-pyrimidinyl]carbamate N-oxide, 50 ml. of ethanol and 10 ml. of 35% aqueous sodium hydroxide solution was allowed to stand at room temperature over the weekend and then was refluxed for four hours, concentrated in vacuo and the concentrate acidified with acetic acid. The mixture was heated on a steam bath and made basic by adding ammonium hydroxide solution. The crystalline solid was collected, washed with water, dried in vacuo at 80° C. and recrystallized from dimethylformamide to yield 3.2 g. of 4-amino-2-(4-pyridinyl)-4-pyrimidine N-oxide, m.p. 317°–320° C.

4-Amino-2-(4-pyridinyl)-4-pyrimidine N-oxide also is prepared following the above procedure of Example A-22 but using in place of n-butyl N-[2-(4-pyridinyl)-4-pyrimidinyl]-carbamate N-oxide a molar equivalent quantity of N-[2-(4-pyridinyl)-4-pyrimidinyl]acetamide N-oxide or ethyl N-[2-(4-pyridinyl)-4-pyrimidinyl]carbamate N-oxide.

A-23. N-(1,1-dimethylethyl)-2-(4-pyridinyl)-4-pyrimidinamine [alternatively can be named 4-tert.-butylamino)-2-(4-pyridinyl)pyrimidine]— A mixture containing 10.2 g. of 4-chloro-2-(4-pyridinyl)pyrimidine, 15 ml. of tert. — butylamine and 50 ml. of ethanol was refluxed for four hours and then concentrated in vacuo to remove the solvent and other volatile materials. The residue was partitioned between chloroform and aqueous ammonium hydroxide solution. The chloroform layer was separated and the chloroform removed in vacuo. The remaining residue was dissolved in ether containing 2 to 5% (v/v) methanol and the solution was passed through a silica gel column. The filtrate was evaporated in vacuo to remove the solvents and the residue was crystallized from cyclohexane to yield 7.1 g. of N-(1,1-dimethylethyl)-2-(4-pyridinyl)-4-pyrimidinamine, m.p. 202°–204° C.

A-24. N,6-Dimethyl-2-(4-pyridinyl)-4-pyrimidinamine, m.p. 145°–146° C., 7.6 g. was prepared following the procedure described in Example A-23 using 8 g. of 4-chloro-2-(4-pyridinyl)-pyrimidine, 15 ml. of 40% aqueous methylamine, 50 ml. of ethanol, a refluxing period of two hours and recrystallization from ethyl-n-hexane.

A-25. 4-Amino-6-n-propyl-2-(4-pyridinyl)pyrimidine is prepared following the procedures described in Examples A-5, A-6 and A-7 starting with a molar equivalent quantity of 6-n-propyl-2-(4-pyridinyl)-4-pyrimidinol in place of 6-methyl-2-(4-pyridinyl)-4-pyrimidinol to produce respectively 4-chloro-6-n-propyl-2-(4-pyridinyl)pyrimidine, 4-hydrazino-6-n-propyl-2-(4-pyridinyl) pyrimidine and 4-amino-6-n-propyl-2-(4-pyridinyl)-pyrimidine.

A-26. N-[2-(4-Pyridinyl)-4-pyrimidinyl]acetamide N-oxide is obtained following the procedure described in Example A-21 using a molar equivalent quantity of N-[2-(4-pyridinyl)-4-pyrimidinyl]acetamide in place of n-butyl N-[2-(4-pyridinyl)-4-pyrimidinyl]carbamate.

A-27. Ethyl N-[2-(4-pyridinyl)-4-pyrimidinyl]-carbamate N-oxide is obtained following the procedure described in Example A-21 using a molar equivalent quantity of ethyl N-[2-(4-pyridinyl)-4-pyrimidinyl]carbamate in place of n-butyl N-[2-(4-pyridinyl)-4-pyrimidinyl]carbamate.

Following the procedure described in Example A-23 using in place of tert.-butylamine a molar equivalent quantity of the appropriate amine of the formula $H_2NR$, the compounds of Examples A-28 through A-31 are obtained:

A-28. N-Ethyl-2-(4-pyridinyl)-4-pyrimidinamine using ethylamine.

A-29. N-(2-Hydroxyethyl)-2-(4-pyridinyl)-4-pyrimidinamine using 2-hydroxyethylamine.

A-30. N-Isopropyl-2-(4-pyridinyl)-4-pyrimidinamine using isopropylamine.

A-31. tert.-Butyl N-[2-(4-pyridinyl)-4-pyrimidinyl]-carbamate is obtained following the procedure used in Example A-19 but using in place of n-butyl chloroformate a molar equivalent quantity of tert.-butyl azidoformate.

B. N—$R_3$—N—$R_4$—N'—R—N'—[2—Q—5—$R_1$—6—$R_2$—4- PYRIMIDINYL]UREAS AND ANALOGS

B-1. N-Ethyl-N'-[2-(4-pyridinyl)-4-pyrimidinyl]urea — To 200 ml. of dimethyl sulfoxide was added 5 g. of 57% (w/w) sodium hydride oil dispersion (as used here and hereinafter means 57% NaH dispersed in mineral oil). To this mixture at room temperature was added with stirring 17 g. of 4-amino-2-(4-pyridinyl)pyrimidine and stirring was continued until the evolution of hydrogen ceased, thereby yielding a solution of the N-sodium salt of said 4-amino compound. To this stirred mixture was added dropwise 7.1 g. of ethyl isocyanate whereupon the reaction temperature rose to about 45° C. The reaction mixture was stirred for an additional sixty minutes after addition of the isocyanate and then allowed to stand at room temperature overnight (about sixteen hours). The reaction mixture was poured into a mixture of ice and water and stirred until the ice melted. The precipitate was collected, washed successively with water and acetonitrile, dried in vacuo at 80° C., recrystallized from ethanol, washed with ether and dried in vacuo at 80° C. to yield 17 g. of N-ethyl-N'-[2L -(4-pyridinyl)-4-pyrimidinyl[urea, m.p. >300° C. after solidifying at 233° C.

B-2. N-Isopropyl-N'-[2-(4-pyridinyl)-4-pyrimidinyl]urea, 17 g., m.p. 220°->300° C., was prepared following the procedure described in Example B-1 using 17 g. of 4-amino-2-(4-pyridinyl)pyrimidine, 8.5 g. of isopropyl isocyanate, 200 ml. of dimethyl sulfoxide, 5 g. of 57% sodium hydride oil dispersion but omitting the standing of the reaction mixture at room temperature overnight.

B-3. N-n-Propyl-N'-[2-(4-pyridinyl)-4-pyrimidinyl]urea, 18.5 g., m.p. 233°->300° C., was prepared following the procedure described in Example B-2 using 17 g. of 4-amino-2-(4-pyridinyl)pyrimidine, 8.5 g. of n-propyl isocyanate, 200 ml. of dimethyl sulfoxide and 5 g. of 57% sodium hydride oil dispersion.

B-4. N-Methyl-N'-[2-(4-pyridinyl)-4-pyrimidinyl]urea, 17.5 g., m.p. 273°->300° C., was prepared following the procedure described in Example B-2 using 17 g. of 4-amino-2-(4-pyridinyl)pyrimidine, 5.7 g. of methyl isocyanate, 200 ml. of dimethyl sulfoxide and 5 g. of 57% sodium hydride oil dispersion.

B-5. N-tert.-Butyl-N'-[2-(4-pyridinyl)-4-pyrimidinyl]urea — A mixture containing 8.6 g. of 4-amino-2-(4-pyridinyl)-pyrimidine, 6.2 g. of tert.-butyl isocyanate and 700 ml. of xylene was refluxed with stirring for one hundred and forty-four hours and then allowed to cool to room temperature. The precipitate was collected and the filtrate evaporated in vacuo to dryness. The residue was combined with the collected precipitate and recrystallized from methanol to yield 7.6 g. of N-tert.-butyl-N'-[2-(4-pyridinyl)-4-pyrimidinyl]urea, m.p. >350° C.

To a warm suspension containing 139 g. of N-tert.-butyl-N'-[2-(4-pyridinyl)-4-pyrimidinyl]urea in one liter of isopropyl alcohol was added 43 ml. of concentrated hydrochloric acid. The resulting solution was cooled in ice. The precipitate was collected, washed successively with cold isopropyl alcohol and then ether, recrystallized from 625 ml. of 95% ethanol using decolorizing charcoal and drying the recrystallized material in vacuo at 60° C. to yield 117 g. of N-tert.-butyl-N'-[2-(4-pyridinyl)-4-pyrimidinyl]urea hydrochloride, m.p. 192° C. with decomposition.

N-tert.-Butyl-N'-[2-(4-pyridinyl)-4-pyrimidinyl]urea also was prepared as follows: A 59 g. portion of 50% sodium hydride oil dispersion under nitrogen was washed with 200 ml. of n-hexane and separated by decantation. To said oil dispersion was added 2 liters of dimethyl sulfoxide followed by portion-wise addition over fifteen minutes of 172 g. of 4-amino-2-(4-pyridinyl)pyrimidine. The resulting mixture was stirred for two hours whereupon most of the evolution of hydrogen had ceased. To the stirred mixture was added dropwise over a fifteen minute period a solution containing 100 g. of tert.-butyl isocyanate in 150 ml. of dimethyl sulfoxide. The exothermic reaction caused the reaction temperature to rise to 45° C. The reaction mixture was then stirred for two hours and poured into 10 liters of ice water. The mixture was stirred for thirty minutes; the precipitate was collected, washed with water and dried in vacuo to yield 243 g. of product. This material was dissolved in 10 liters of boiling absolute ethanol, filtered hot, the filtrate cooled in an ice bath, and the crystalline product collected, washed successively with cold ethanol and ether to give 215 g. of N-tert.-butyl-N'-[2-(4-pyridinyl)-4-pyrimidinyl]urea.

A solution of 99 g. of N-tert.-butyl-N'-[2-(4-pyridinyl)-4-pyrimidinyl]urea in 1 liter of 95% ethanol was treated with 36 g. of 98% methanesulfonic acid. The precipitate was collected to yield 113 g. of N-tert.-butyl-N'-[2-(4-pyridinyl)-4-pyrimidinyl]urea methanesulfonate. When this salt was treated with water, momentarily a solution formed but then a heavy precipitation occurred. Apparently the salt reverted to the free base form. The above-disclosed hydrochloride salt also reverts to the free base form in water alone. A sample of the free base form was readily dissolved in 85% lactic acid with slight warming to form a solution of the lactate salt of N-tert.-butyl-N'-[2-(4-pyridinyl)-4-pyrimidinyl]urea. When this solution was diluted with water, no precipitate formed.

B-6. N-n-Hexyl-N'-[2-(4-pyridinyl)-4-pyrimidinyl]-urea, 14.5 g., m.p. 168°–169° C., was obtained following the procedure described in Example B-2 using 17 g. of 4-amino-2-(4-pyridinyl)pyrimidine, 12.7 g. of n-hexyl isocyanate, 200 ml. of dimethyl sulfoxide and 5 g. of 57% sodium hydride oil dispersion.

B-7. N-Cyclohexyl-N'-[2-(4-pyridinyl)-4-pyrimidinyl]-urea, 19.5 g., m.p. 253°–>300° C., was prepared following the procedure described in Example B-2 using 17 g. of 4-amino-2-(4-pyridinyl)pyrimidine, 12.5 of g. cyclohexyl isocyanate, 200 ml. of dimethyl sulfoxide and 5 g. of 57% sodium hydride oil dispersion.

B-8. N-n-Butyl-N'-[2-(4-pyridinyl)-4-pyrimidinyl]-urea — A mixture containing 8.6 g. of 4-amino-2-(4-pyridinyl)-pyrimidine, 7.2 g. of n-butyl isocyanate, 100 ml. of dimethyl sulfoxide and 2.5 g. of 57% sodium hydride oil dispersion was stirred in an ice bath for one hour and then at room temperature for two hours. Since no reaction had yet taken place as indicated by t.l.c. analysis, it was warmed on a steam bath with stirring whereupon there was a vigorous evolution of hydrogen yielding a clear solution. This reaction mixture was allowed to stand at room temperature for two hours and then poured into ice cold water. The white solid was collected, washed successively with water and ether, dried in vacuo at 80° C. and recrystallized from ethanol to yield 5.6 g. of N-n-butyl-N'-[2-(4-pyridinyl)-4-pyrimidinyl]-urea, m.p. 210°–212° C.

B-9. N-n-Butyl-N'-[2-(3-pyridinyl)-4-pyrimidinyl]-urea, 3.4 g., m.p. 180°–182° C., was prepared like the procedure described in Example B-8 using 8.8 g. of 4-amino-2-(3-pyridinyl)-pyrimidine, 5.1 g. of n-butyl isocyanate, 2.4 g. of 57% sodium hydride oil dispersion, 100 ml. of dimethyl sulfoxide, a reaction period of five hours at room temperature with stirring followed by standing at room temperature overnight (about sixteen hours), pouring the reaction mixture in water, making the mixture acidic with acetic acid, collecting the solid, washing the solid with ether and recrystallizing it from isopropyl alcohol.

B-10. N-tert.-Butyl-N'-[2-(3-pyridinyl)-4-pyrimidinyl]-urea, 11.2 g., m.p. 260°–261° C., was prepared like the procedure described in Example B-9 using 8.6 g. of 4-amino-2-(3-pyridinyl)-pyrimidine, 2.4 g. of 57% sodium hydride oil dispersion, 50 ml. of dimethyl sulfoxide, 5 g. of tert.-butyl isocyanate and also heating the reaction mixture with stirring on a water bath at 50° C. for thirty minutes and not recrystallizing the solid product but washing it with water and drying it in vacuo at 80° C.

B-11. N-Isopropyl-N'-[2-(3-pyridinyl)-4-pyrimidinyl]-urea — A mixture containing 4.8 g. of 57% sodium hydride oil dispersion, 17.2 g. of 4-amino-2-(3-pyridinyl)-pyrimidine and 100 ml. of dimethyl sulfoxide was stirred for twenty-five minutes and to this mixture was added 10 g. of isopropyl isocyanate and the resulting mixture was stirred for five hours and then poured into ice cold water. The mixture was made acidic by adding acetic acid. The solid was collected, washed successively with water and n-hexane, and then recrystallized from ethanol to yield 17.9 g. of N-isopropyl-N'-[2-(3-pyridinyl)-4-pyrimidinyl]urea, m.p. 224°–225° C.

B-12. N-Ethyl-N'-[2-(3-pyridinyl)-4-pyrimidinyl]-urea, 11.5 g., m.p. 220°–222° C., was prepared like the procedure described in Example B-8 using 15 g. of 4-amino-2-(3-pyridinyl)-pyrimidine, 75 ml. of dimethyl sulfoxide, 15 ml. of ethyl isocyanate, 4.8 g of 57% sodium hydride oil dispersion, a reaction period of four hours at room temperature with stirring and then allowing the reaction mixture to stand at room temperature overnight.

B-13. N-tert.-Butyl-N'-[5-methyl-2-(4-pyridinyl)-4-pyrimidine]urea — A mixture containing 9.3 g. of 4-amino-5-methyl-2-(4-pyridinyl)-pyrimidine, 2.4 g. of 57% sodium hydride oil dispersion, 5.6 g. of tert.-butyl isocyanate and 100 ml. of dimethyl sulfoxide was stirred on a water bath at 50° C. for six hours and then poured into 600 ml. of ice cold water. To the mixture was added 6 ml. of glacial acetic acid. The separated solid was collected, washed with ether and recrystallized from ethanol to yield 10.4 g. of N-tert.-butyl-N'-[5-methyl-2-(4-pyridinyl)-4-pyrimidine[urea, m.p. 227°–228° C. with decomposition.

B-14. N-tert.-Butyl-N'-[2-(2-pyridinyl)-4-pyrimidinyl]urea, 18.6 g., m.p. 223°–225° C., was prepared following the procedure described in Example B-13 using 17.2 g. of 4-amino-2-(2-pyridinyl)pyrimidine, 4.8 g. of 57% sodium hydride oil dispersion, 10 g. of tert.-butyl isocyanate, 200 ml. of dimethyl sulfoxide, a reaction period of seven hours on a water bath at 50° C., pouring the reaction mixture into 500 ml. of ice cold water, adding 8 ml. of glacial acetic acid, collecting the white precipitate, washing it successively with water and ether and then recrystallizing it from isopropyl alcohol.

B-15. N,N-Diethyl-N'-[2-84-pyridinyl)-4-pyrimidinyl]-urea — A mixture containing 17.2 g. of 4-amino-2-(4-pyridinyl)-pyrimidine, 4.8 g. of 57% sodium hydride oil dispersion and 75 ml. of dimethyl sulfoxide was stirred for thirty minutes at room temperature and then 6 g. of N,N-diethylcarbamyl chloride was added dropwise with stirring and cooling in an ice bath. After said addition had been completed, the reaction mixture was stirred in an ice bath for three hours and then at room temperature for one hour. The reaction mixture was next poured into ice cold water whereupon only a small amount of the solid separated. The aqueous mixture was made basic by adding ammonium hydroxide solution and the basic mixture was extracted with chloroform. The chloroform solution was concentrated in vacuo to yield an oily residue which was triturated with ether. The resulting solid was collected, washed with isopropyl alcohol and dried in vacuo at 80° C. The solid was then treated with boiling ethanol, the insoluble material filtered off and the filtrate concentrated to dryness to give 4.8 g. of N,N-diethyl-N'-[2-(4-pyridinyl)-4-pyrimidinyl]-urea, m.p. 165°–166° C.

B-16. N-[2-(4-Pyridinyl)-4-pyrimidinyl]urea — A mixture containing 12 g. of 4-amino-2-(4-pyridinyl)-pyrimidine, 3.2 g. of 57% sodium hydride oil dispersion and 75 ml. of dimethylformamide was stirred until the reaction was completed. Then 12.2 g. of 1,1'-carbonyldiimidazole was added and the reaction mixture was stirred for forty-five minutes. To the reaction mixture containing N-[2-(4-pyridinyl)-4-pyrimidinyl]-imidazole-1-carboxamide was added 15 g. of ammonium acetate followed by the addition of 10 ml. of 30% aqueous ammonium hydroxide solution and stirring of the mixture at room temperature was continued overnight. The dimethylformamide was distilled off in vacuo and the remaining material was diluted with water. The solid was collected, washed with water and dried in vacuo at 80° C. and then recrystallized three times from dimethylformamide-ethanol to yield 3.9 g. of N-[2-(4-pyridinyl)-4-pyrimidinyl]urea, m.p. >300° C.

B-17. N-(3-Amyl)-N′-[2-(4-pyridinyl)-4-pyrimidinyl]-urea — A mixture of 4.8 g. of 57% sodium hydride oil dispersion, 75 ml. of dimethylformamide and 17 g. of 4-amino-2-(4-pyridinyl)pyrimidine was stirred until the evolution of hydrogen stopped. This solution was then added slowly to a stirred solution containing 19.5 g. of 1,1′-carbonyldiimidazole and 75 ml. of dimethylformamide, the resulting mixture was stirred for thirty minutes. Then to this mixture was added 10.2 g. of 3-amylamine (same as 3-aminopentane), the resulting reaction mixture was stirred for two hours, 10 ml. of acetic acid was added and the mixture was poured into ice cold water. The solid was collected, washed succesively with water and ether, and then dried in vacuo at 80° C. to yield 25.3 g. of N-(3-amyl)-N′-[2-(4-pyridinyl)-4-pyrimidinyl]urea, m.p. 206°–209° C.

This compound was converted into its dimethanesulfonate salt as follows: The compound was dissolved in 300 ml. of boiling ethanol and filtered. To the hot filtrate was added 13 g. of methanesulfonic acid and the resulting solution was allowed to stand at room temperature. The resulting white precipitate was collected, washed successively with ethanol and ether, and dried in vacuo at 80° C. to yield 17.2 g. of N-(3-amyl)-N′-[2-(4-pyridinyl)-4-pyrimidinyl]urea as its dimethanesulfonate, m.p. 147°–149° C.

B-18. N-tert.-Butyl-N′-[2-(4-pyridinyl)-4-pyrimidinyl]-urea N-oxide — A mixture containing 15 g. of N-tert.-butyl-N′-[2-(4-pyridinyl)-4-pyrimidinyl]-urea, 15 g. of 85% m-chloroperbenzoic acid and 500 ml. of chloroform was stirred at room temperature for five hours and evaporated to dryness. The residue was stirred with 20 ml. of 10% aqueous potassium carbonate solution. The yellow solid was collected, washed with water and dried in vacuo at 80° C., digested with boiling ethanol, collected and dried in vacuo at 80° C. to yield 13.1 g. of N-tert.-butyl-N′-[2-(4-pyridinyl)-4-pyrimidinyl]urea N-oxide, m.p. >300° C. with decomposition.

Alternatively, N-tert.-butyl-N′-[2-(4-pyridinyl)-4-pyrimidinyl]urea N-oxide is prepared following the procedure of Example B-2 using a molar equivalent quantity of 4-amino-2-(4-pyridinyl)pyrimidine N-oxide (see Example A-22 for preparation) in place of 4-amino-2-(4-pyridinyl)pyrimidine and a molar equivalent quantity of tert.-butyl isocyanate in place of isopropyl isocyanate.

B-19. N-Isopropyl-N′-[2-(4-pyridinyl)-4-pyrimidinyl]-urea N-Oxide — To a stirred mixture containing 10.2 g. of N-isopropyl-N′-[2-(4-pyridinyl)-4-pyrimidinyl]urea and 500 ml. of chloroform was added 8 g. of 85% m-chloroperbenzoic acid and the resulting solution was allowed to stand at room temperature for four hours. To the reaction mixture was added 100 ml. of 10% aqueous potassium carbonate solution and the mixture was stirred for thirty minutes. The yellow solid was collected and washed with water. The chloroform layer was separated, evaporated in vacuo and the residue was combined with said yellow solid. The combined solid was suspended in 150 ml. of isopropyl alcohol, 5 g. of methanesulfonate acid was added and the mixture was heated to form a clear solution. On cooling to room temperature there separated a crystalline solid which was collected, washed with isopropanol and dried in vacuo at 80° C. to yield 12.7 g. of N-isopropyl-N′-[2-(4-pyridinyl)-4-pyrimidine]urea N-oxide as its dimethanesulfonate, m.p. 125°–150° C.

Following the procedure described in Example 2 but using in place of 4-amino-2-(4-pyridinyl)pyrimidine a molar equivalent quantity of the appropriate 4-amino-2-(4-pyridinyl)-5—$R_1$—6—$R_2$—pyrimidine and in place of isopropyl isocyanate a molar equivalent quantity of tert.-butyl isocyanate, the compounds of Examples B-20 through B-23 are obtained:

B-20. N-tert.-Butyl-N′-[6-methyl-2-(4-pyridinyl)-4-pyrimidinyl]urea using 4-amino-6-methyl-2-(4-pyridinyl)-pyrimidine.

B-21. N-tert.-Butyl-N′-[6-n-propyl-2-(4-pyridinyl)-4-pyrimidinyl]urea using 4-amino-6-n-propyl-2-(4-pyridinyl)-pyrimidine.

B-22. N′-[5-Ethyl-2-(4-pyridinyl)-4-pyrimidinyl]-N-(tert.-butyl)urea using 4-amino-5-ethyl-2-(4-pyridinyl)-pyrimidine.

B-23. N′-[5-Cyano-2-(4-pyridinyl)-4-pyrimidinyl]-N-(tert.-butyl)urea using 4-amino-5-cyano-2-(4-pyridinyl)-pyrimidine.

Following the procedure described in Example B-17 first reacting an N-R-2-(4-pyridinyl)-4-pyrimidinamine as its N-sodium salt with 1,1′-carbonyldiimidazole to produce N-R-N-[2-(4-pyridinyl)-4-pyrimidinyl]-imidazole-1-carboxamide and then reacting said 1-carboxamide with a molar equivalent quantity of the appropriate amine ($R_3R_4NH$) in place of 3-amylamine, there are obtained the compounds of Examples B-24 through B-35.

B-24. N,N,N′-Trimethyl-N′-[2-(4-pyridinyl)-4-pyrimidinyl]urea first using N-methyl-2-(4-pyridinyl)-4-pyrimidinamine to produce N-methyl-N-[2-(4-pyridinyl)-4-pyrimidinyl]imidazole-1-carboxamide and then reacting it with dimethylamine.

B-25. N′-Ethyl-N-isopropyl-N′-[2-(4-pyridinyl)-4-pyrimidinyl]urea first using N-ethyl-2-(4-pyridinyl)-4-pyrimidinamine to obtain N-ethyl-N-[2-(4-pyridinyl)-4-pyrimidinyl]-imidazole-1-carboxamide and then reacting it with isopropylamine.

B-26. N-Ethyl-N′-isopropyl-N-methyl-N′-[2-(4-pyridinyl)-4-pyrimidinyl]urea first using N-isopropyl-2-(4-pyridinyl-4-pyrimidinamine to produce N-isopropyl-N-[2-(4-pyridinyl)-4-pyrimidinyl]imidazole-1-carboxamide and then reacting it with N-ethyl-N-methylamine.

B-27. N′-tert.-Butyl-N-ethyl-N′-[2-(4-pyridinyl)-4-pyrimidinyl]urea is prepared first using N-tert.-butyl-2-(4-pyridinyl)-4-pyrimidinamine to produce N-tert.-butyl-N-[2-(4-pyridinyl)-4-pyrimidinyl]imidazole-1-carboxamide and then reacting it with ethylamine.

B-28. N-tert.-Butyl-N′-methyl-N′-[2-(4-pyridinyl)-4-pyrimidinyl]urea is obtained first using N-methyl-2-(4-pyridinyl)-4-pyrimidinamine to produce N-methyl-N-[2-(4-pyridinyl)-4-pyrimidinyl]imidazole-1-carboxamide and then reacting it with tert.-butylamine.

B-29. N-(2-Hydroxyethyl)-N′-methyl-N′-[2-(4-pyridinyl)-4-pyrimidinyl]urea is obtained first using N-methyl-2-(4-pyridinyl)-4-pyrimidinamine to produce N-methyl-N-[2-(4-pyridinyl)-4-pyrimidinyl]imidazole- 1-carboxamide and reacting it with 2-hydroxyethylamine.

B-30. N'-Ethyl-N,N-bis(2-hydroxyethyl)-N'-[2-(4-pyridinyl)-4-pyrimidinyl]urea is obtained first using N-ethyl-2-(4-pyridinyl)-4-pyrimidinamine to produce N-ethyl-N-[2-(4-pyridinyl)-4-pyrimidinyl]imidazole-1-carboxamide and then reacting it with N,N-bis(2-hydroxyethyl)amine.

B-31. N,N-bis(2-Hydroxyethyl)-N'-[2-(4-pyridinyl)-4-pyrimidinyl]urea is obtained first using 2-(4pyridinyl)-4-pyrimidinamine to produce N-[2-(4-pyridinyl)-4-pyrimidinyl]-imidazole-1carboxamide and then reacting it with N,N-bis(2-hydroxyethylamine).

B-32. N,N-bis(2-Hydroxyethyl)-N'-methyl-N'-[2-(4-pyridinyl)-4-pyrimidinyl]urea is obtained first using N-methyl-2-(4-pyridinyl)-4-pyrimidinamine to produce N-methyl-N-[2-(4-pyridinyl)-4-pyrimidinyl]imidazole-1-carboxamide and then reacting it with N,N-bis(2-hydroxyethyl)amine.

B-33. N-(2-Hydroxy-1,1-dimethylethyl)-N'-[2-(4-pyridinyl)-4-pyrimidinyl]urea is obtained first using 2-(4-pyridinyl)-4-pyrimidinamine to produce N-[-(4-pyridinyl)-4-pyrimidinyl]imidazole-1-carboxamide and then reacting it with N-(2-hydroxy-1,1-dimethylethyl)amine.

B-34. N-Cyclopropyl-N'-[2-(4-pyridinyl)-4-pyrimidinyl]-urea is obtained first using 2-(4-pyridinyl)-4-pyrimidinamine to produce N-[2-(4-pyridinyl)-4-pyrimidinyl]imidazole-1-carboxamide and then reacting it with cyclopropylamine.

B-35. N-Cyclopentyl-N'-[2-(4-pyridinyl)-4-pyrimidinyl]urea is obtained first using 2-(4-pyridinyl)-4-pyrimidinamine to produce N-[2-(4-pyridinyl)-4-pyrimidinyl]-imidazole-1carboxamide and then reacting it with cyclopentylamine.

Following the procedure described in Example 2 using in place of 4-amino-2-(4-pyridinyl)pyrimidine a molar equivalent quantity of the appropriate 4-amino-2-Q-pyrimidine and in place of isopropyl isocyanate a molar equivalent quantity of tert.-butyl isocyanate, the compounds of Examples B-36 through B-41 are obtained.

B-36. N-Allyl-N'-[2-(4-pyridinyl)-4-pyrimidinyl]-urea is obtained using 4-amino-2-(4-pyridinyl)pyrimidine and allyl isocyanate.

B-37. N-(2-Methyl-2-propenyl)-N'-[2-(4-pyridinyl)-4pyrimidinyl]urea is obtained using 4-amino-2-(4-pyridinyl)-pyrimidine and 2-methyl-2-propenyl isocyanate.

B-38. N-tert.-Butyl-N'-[2-(2-methyl-4-pyridinyl)-4pyrimidinyl]urea is obtained using 4-amino-2-(2-methyl-4-pyridinyl)pyrimidine and tert.-butyl isocyanate.

B-39. N-tert.-Butyl-N'-[2-(3-methyl-4-pyridinyl)-4-pyrimidinyl]urea is obtained using 4-amino-2-(3-methyl-4-pyridinyl)pyrimidine and tert.-butyl isocyanate.

B-40. N-tert.-Butyl-N'-[2-(2-ethyl-4-pyridinyl)-4-pyrimidinyl]urea is obtained using 4-amino-2-(2-ethyl-4-pyridinyl)pyrimidine and tert.-butyl isocyanate.

B-41. N-tert.-Butyl-N'-[2-(2,6-dimethyl-4pyridinyl)-4-pyrimidinyl]urea is obtained using 4-amino-2-(2,6-dimethyl-4-pyridinyl)pyrimidine and tert.-butyl isocyanate.

The anti-allergic activity of the compounds of formula I is determined by showing their effectiveness as inhibitors of release of mediators of allergic reactions by the IgE-mediated passive cutaneous anaphylaxis (PCA) method described as follows (IgE is the abbreviation for Immunoglobulin E, the cell-sensitizing antibody):

Sprague-Dawley rats weighing 70 to 90 grams each are injected intradermally with multiple serial dilutions of IgE forty-eight hours before administration of the drug. The rats are fasted overnight (approximately seventeen hours) before the drug administration. Each drug being tested is administered orally at 100 mg./kg. to each of four rats. Six other rats are observed as a control group. One hour after drug administration, 10 mg./kg. of egg albumen was administered intravenously together with 17 mg./kg. of Evans Blue. Thirty minutes later, the rats are killed by cervical fracture, the i.d. injected skin is everted, and the average of two perpendicular diameters of each blue area is recorded. The average diameters vs. the reciprocal of the dilution of antibody in the control group is plotted on a semilog graph, and a best-fitting line is drawn through points for the control rats, and a best-fitting parallel line to the control line is drawn for each tested drug. Comparative drug activity is evaluated by the degree of the shift to the right from controls, that is, by the ratio, R, of:

$$R = \frac{\text{reciprocal of antibody dilution necessary for zero mm. diameter in control group}}{\text{reciprocal of antibody dilution necessary for zero mm. diameter in medicated group}}$$

The results are interpreted as follows:

| R( = degree of shift to the right) | Interpretation of Drug Activity |
| --- | --- |
| 1.0 – 2.0 | Inactive |
| 2 – 4 | Weak |
| 4 – 8 | Moderate |
| >8 | Strong |

When tested by the above procedure, said compounds of formula I were found to have R values >2, the more active and preferred compounds having R values of >8 and >10.

The more active and preferred compounds are further evaluated at multiple doses, e.g., 100, 25, 6.2 and 1.6 mg./kg., by the IgE-mediated PCA in rats. The test procedure for each dose is the same as given above, except for the interpretation of results. If two or more doses of a compound have response lines (diameter vs. antibody dilution) that are parallel to each other and to controls, the potency of such a compound is expressed by $d(Ab)_3$, that is, the dose of a drug that would necessitate tripling of the concentration of antibody for the control rats in order to achieve the same response line as for the medicated rats. The $d(Ab)_3$ value is calculated as follows: The "R" values are plotted vs. the doses in mg./kg. on a log-log graph. A best-fitting line is drawn through the points, and a dose in mg./kg. corresponding to R=3 is read as the $d(Ab)_3$. The hereinabove-noted preferred embodiments, when tested by said procedure, were found to have $d(Ab)_3$ values ranging from about 2 to 12, the lower the value the more active the compound.

The actual determination of the numerical anti-allergic data definitive for a particular compound of the invention is readily obtained according to the above-described standard test procedures by technicians versed in pharmacological test procedures, without any need for any extensive experimentation.

The compounds of the invention can ordinarily be prepared for use by dissolving under sterile conditions a salt form of the compounds in water (or an equivalent amount of a non-toxic acid if the free base is used), or in a physiologically compatible aqueous medium such as saline, and stored in ampules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Also, the compounds can be formulated for oral administration in aqueous alcohol, glycol or oil solutions or oil-water emulsions in the same manner as conventional medicinal substances are prepared.

We claim:

1. The process for preparing a compound of the formula

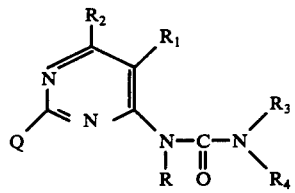

where Q is 4- or 3- or 2-pyridinyl or 4- or 3- or 2-pyridinyl having one or two lower-alkyl substituents or N-oxide thereof, R is hydrogen or lower-alkyl, $R_1$ is hydrogen, lower-alkyl or cyano, $R_2$ is hydrogen or lower-alkyl, $R_3$ is hydrogen, lower-alkyl or lower-hydroxyalkyl, $R_4$ is hydrogen, lower-alkyl, lower-hydroxyalkyl, lower-alkenyl or lower-cycloalky, which comprises reacting a 2—Q—4—RNH—5—$R_1$—6—$R_2$-pyrimidine with 1,1'-carbonyldiimidazole to produce N—(-2—Q—5—$R_1$—6—$R_2$—4—pyrimidinyl)-N-R-imidazole-1-carboxamide and then reacting said 1-carboxamide with $R_3R_4NH$ to produce a compound of the formula

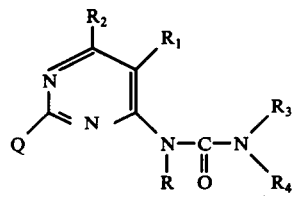

where $R_3$ and $R_4$ have the meanings given above.

2. The process according to claim 1 which comprises reacting a 2—Q—4—RNH—5—$R_1$—6—$R_2$—pyrimidine with 1,1'-carbonyl-diimidazole to produce N—(-2—Q—5—$R_1$—6—$R_2$—4—pyrimidinyl)-N-R-imidazole-1-carboxamide and then reacting said 1-carboxamide with $R_3R_4NH$ to produce a compound of the formula

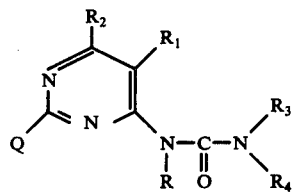

where Q is 4-pyridinyl or 3-pyridinyl, and R, $R_1$, $R_2$, $R_3$ and $R_4$ are defined as in claim 1.

3. The process according to claim 2 where R, $R_1$ and $R_2$ are each hydrogen, and $R_3$ and $R_4$ are each hydrogen or lower-alkyl.

* * * * *

UNITED STATES PATENT AND TRADEMARK OFFICE
CERTIFICATE OF CORRECTION

PATENT NO. : 4,053,475
DATED : October 11, 1977
INVENTOR(S) : George Y. Lesher and Baldev Singh It is certified that error appears in the above-identified patent and that said Letters Patent are hereby corrected as shown below:

Column 4, line 17, "or" should read -- of --.

Column 4, line 59, "Prepared" should read -- Preferred --.

Column 5, line 11, "salts" should read -- salt --.

Column 5, lines 57 and 58, "pyramidine" should read -- pyrimidine --.

Column 6, line 4, "$R_2$", second occurrence, should read -- $R_1$ --.

Column 6, line 7, "thylenemalonitrile" should read -- thylenemalononitrile --; and, "ethoxymethylenemaloni" should read -- ethoxymethylenemalononi --.

Column 6, line 28, "pepared" should read -- prepared --.

Column 19, line 33, "N-(-" should read -- N- --; and line 34, "2-" should read -- (2- --.

Column 20, line 15, "N-(-" should read -- N- --; and line 16, "2-" should read -- (2- --.

Signed and Sealed this

Thirteenth Day of June 1978

[SEAL]

Attest:

RUTH C. MASON
Attesting Officer

DONALD W. BANNER
Commissioner of Patents and Trademarks